(12) United States Patent
Kitani et al.

(10) Patent No.: US 9,097,705 B2
(45) Date of Patent: Aug. 4, 2015

(54) EFFICIENT PROLIFERATION METHOD FOR A KUPFFER CELL AND USE THEREOF

(75) Inventors: Hiroshi Kitani, Tsukuba (JP); Takato Takenouchi, Tsukuba (JP); Noriko Yamanaka, Tsukuba (JP); Miyako Yoshioka, Tsukuba (JP)

(73) Assignee: NATIONAL INSTITUTE OF AGROBIOLOGICAL SCIENCES, Tsukuba-shi (JP)

( * ) Notice: Subject to any disclaimer, the term of this patent is extended or adjusted under 35 U.S.C. 154(b) by 407 days.

(21) Appl. No.: 13/500,847

(22) PCT Filed: Oct. 8, 2010

(86) PCT No.: PCT/JP2010/067767
§ 371 (c)(1),
(2), (4) Date: Apr. 6, 2012

(87) PCT Pub. No.: WO2011/043469
PCT Pub. Date: Apr. 14, 2011

(65) Prior Publication Data
US 2012/0202197 A1    Aug. 9, 2012

(30) Foreign Application Priority Data

Oct. 9, 2009   (JP) ................................. 2009-235052

(51) Int. Cl.
*C12N 5/0786* (2010.01)
*A61K 35/407* (2006.01)
*G01N 33/50* (2006.01)

(52) U.S. Cl.
CPC .......... *G01N 33/5055* (2013.01); *C12N 5/0645* (2013.01); *A61K 35/407* (2013.01); *C12N 2500/84* (2013.01)

(58) Field of Classification Search
CPC ................. A61K 2035/124; A61K 2039/515; A61K 35/407; C12N 5/0645; C12N 2502/14; C12N 5/067; C12N 2502/1157; C12N 2503/02; C12N 2500/84; C12Q 1/00
USPC ................... 424/93.7; 435/29, 373, 467, 7.21
See application file for complete search history.

(56) References Cited

FOREIGN PATENT DOCUMENTS

JP    2006-296252 A    11/2006
WO    02/059279 A2    8/2002

OTHER PUBLICATIONS

Zinchenko et al. Hepatocyte and Kupffer Cells Co-cultured on Micropatterned Surfaces to Optimize Hepatocyte Function. Tissue Engineering vol. 12, No. 4, 2006. p. 751-761.*
Landmann-Suter. Generation and Use of a Mouse Kupffer Cell Line. Altex 24, Special Issue 2007. p. 42-45.*
Acosta et al. Primary Monolayer Cultures of Postnatal Rat Liver Cells With Extended Differentiated Functions. In Vitro vol. 14, No. 5, 1978. p. 428-436.*
Kitani et al. A novel isolation method for macrophage-like cells from mixed primary cultures of adult rat liver cells. Journal of Immunological Methods 360 (2010) 47-55.*
Alabraba, E. B. et al., "A new approach to isolation and culture of human Kupffer cells," Journal of Immunological Methods, 2007, pp. 139-144, vol. 326.
Bartlett, P. F. et al., "Immortalization of mouse neural precursor cells by the c-*myc* oncogene", PNAS 1988, pp. 3255-3259, vol. 85.
Froh, M. et al., "New Method of Delivering Gene-Altered Kupffer Cells to Rat Liver: Studies in an Ischemia-Reperfusion Model", Gastroenterology, 2003, pp. 124, 172-183.
Heuff, G. et al., "Isolation of rat and human Kupffer cells by a modified enzymatic assay", Journal of Immunological Methods, 1994, pp. 61-65, vol. 174.
Higuchi, H. et al, "Kupffer Saibo no Bunri Baiyo Hoho to sono Kino Kaisekiho," Kan-Tan-Sui, Dec. 28, 1997, pp. 865-871, vol. 35, No. 6.
Handa, H., "Application of Affinity Nano-particles to Medical Field", Acta Obstetrica et Gynaecologica Japonica, 2004, pp. 498-502, vol. 56, No. 9.
Handa, H., "Analysis with affinity beads", Landfall, pp. 1-6, vol. 42, 2001.
Kishie, T. et al., Macrophage Jikken Manual, 3rd print, 1994, pp. 28-35.
Kitani, H. et al., "Kongo Baiyo-kei o Mochiita Kupffer Saibo no Atarashii Tanri Kaishu Hoho", Dai 149 Kai Japanese Society of Veteriany Science Gakujutsu Shukai Koen Yoshishu, Mar. 1, pp. 301, IP-17, 2010.
Mizuno, K. et al., "Motogenic Action of Hepatocyte Growth Factor on Liver Cells in Primary Culture", The Showa University Journal of Medixal Science, 2003, No. 2, pp. 89-98, vol. 15.
Namieno, T. et al., "Co-cultured endothelial and Kupffer cells regulate hepatocyte replication", International Journal of Oncology, 1996, No. 4, pp. 737-740, vol. 9.
Olynyk, J.K. et al., "Isolation and primary culture of rat Kupffer cells", Journal of Gastroenterology Hepatology, 1998, pp. 842-845, vol. 13.
Scharf, J. G. et al., "Regulation of the Components of the 150 kDa IGF Binding Protein Complex in Cocultures of Rat Hepatocytes and Kupffer Cells by 3',5'-Cyclic Adenosine Monophosphate," Journal of Cellular Physiology, 2001, pp. 425-436, vol. 186.
Suzumura, A. et al., "MHC antigen expression on bulk isolated macrophage-microglia from newborn mouse brain: induction of Ia antigen expression by $\gamma$-interferon," Journal of Neuroimmunology, 1987, pp. 263-278, vol. 15.
Suzumura, A., "Culture Technique of Nervous Tissues," Experimental Medicine Separate Volume, Chapter 1, 1995.
Takenouchi, T. et al., "Inhibitory effects of U73122 and U73343 on $Ca^{2+}$ influx and pore formation induced by the activation of P2X7 nucleotide receptors in mouse microglia cell line", Biochimica et Biophysica Acta, 1726, pp. 177-186.

(Continued)

*Primary Examiner* — Taeyoon Kim
(74) *Attorney, Agent, or Firm* — Sughrue Mion, PLLC

(57) ABSTRACT

The present invention has successfully established a mixed culture system capable of actively proliferating a Kupffer cell in a primary culture of a cell population derived from a liver. Additionally, the present invention has successfully established a novel production method for efficiently producing a large amount of highly purified Kupffer cells using this mixed culture system.

9 Claims, 17 Drawing Sheets
(13 of 17 Drawing Sheet(s) Filed in Color)

(56) References Cited

OTHER PUBLICATIONS

Valatas, V et al., "Isolation of rat Kupffer cells: a combined methodology for highly purified primary cultures," Cell Biology International, 2003, pp. 67-73, vol. 27.

International Search Report dated Dec. 14, 2010 in corresponding Japanese Application No. PCT/JP2010/067767.
English translation of International Preliminary Report on Patentability for PCT/JP2010/067767 dated May 24, 2012.

\* cited by examiner

Fig. 5
A
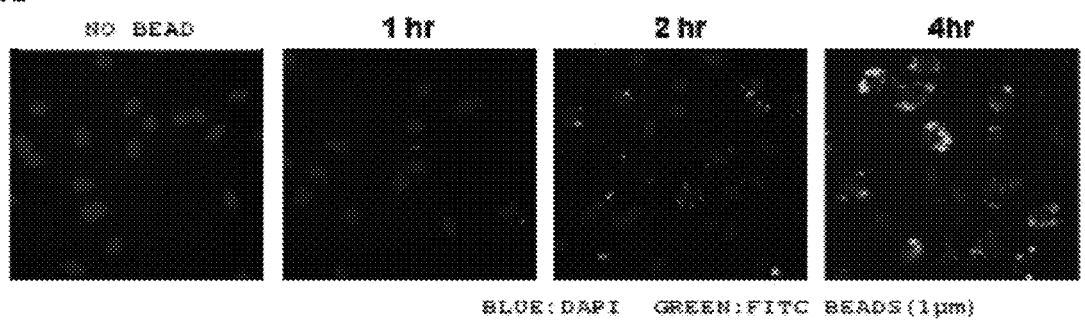
B
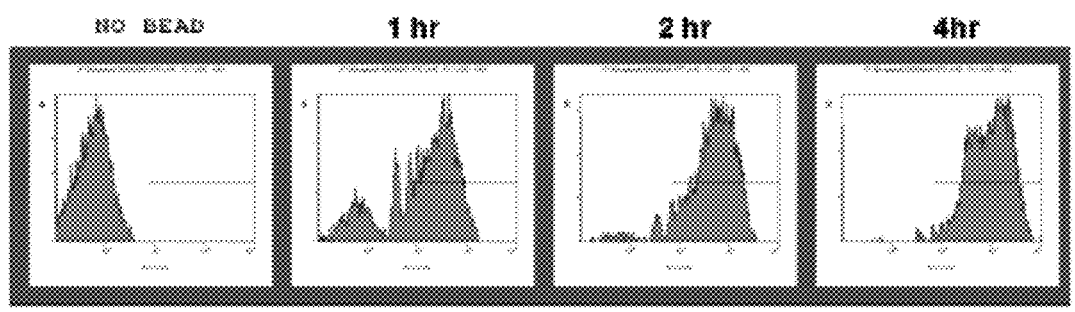

Bar:100μm

EFFICIENT PROLIFERATION METHOD FOR A KUPFFER CELL AND USE THEREOF

CROSS REFERENCE TO RELATED APPLICATIONS

This application is a National Stage of International Application No. PCT/JP2010/067767 filed Oct. 8, 2010, claiming priority based on Japanese Patent Application No. 2009-235052 filed Oct. 9, 2009, the contents of all of which are incorporated herein by reference in their entirety.

TECHNICAL FIELD

The present invention relates to an efficient proliferation method for a Kupffer cell and use thereof. More specifically, the present invention relates to an efficient proliferation method for a Kupffer cell in a mixed culture system, a method for producing a Kupffer cell using the proliferation method, a screening method for a compound influencing proliferation of a Kupffer cell and a screening method for a compound influencing a biological activity of a Kupffer cell, as well as the use of a Kupffer cell produced by the production method.

BACKGROUND ART

Kupffer cells are one type of liver-specific resident tissue macrophages, and are cells playing important biological defense functions such as recognition of foreign materials and induction of immune responses. Moreover, Kupffer cells are closely associated with induction and onset of liver dysfunction, hepatitis, cirrhosis, and the like. Thus, Kupffer cells are considered to be a very important target for elucidating the liver disease state, developing therapeutic drugs, and so forth. For these reasons, many attempts have been made so far to isolate Kupffer cells from livers, and to proliferate isolated Kupffer cells by culturing in vitro.

As a result, as the method for isolating Kupffer cells, methods have been established in which: a cell suspension obtained through liver perfusion with a digestive enzyme such as a collagenase and cell dispersion is centrifuged at a low speed to remove hepatic parenchymal cells, and a Kupffer cell fraction is harvested from non-parenchymal cells in a supernatant on the basis of the cell density using an elutriation centrifuge (Non Patent Literatures 1 to 3). However, the isolation of Kupffer cells has problems to be solved because it requires special equipment, and furthermore complicated processes dependent on skilled techniques. Moreover, each time Kupffer cells are isolated, an animal has to be sacrificed to isolate Kupffer cells from the liver thereof. This makes it difficult to obtain a large amount of Kupffer cells conveniently.

Meanwhile, there is known a method for separating Kupffer cells from liver cells by utilizing the adherence of the Kupffer cells to a plastic dish (Non Patent Literature 4). However, this method also has difficulty obtaining a large amount of Kupffer cells conveniently because the amount of Kupffer cells obtained depends on the amount of liver that is the starting material. In addition, the proliferation ability of Kupffer cells is known to be low. Even if Kupffer cells can be separated by this method, it is still difficult to produce a large amount of Kupffer cells conveniently.

Further, there is known a method in which cells derived from the liver are subjected to limiting dilution and cultured in vitro in the presence of various cytokines and the like to obtain Kupffer cell clones (Patent Literature 1). However, this method requires culturing for quite a long period such as 120 days to obtain a large amount of Kupffer cells. In addition, since the proliferation ability of Kupffer cells is known to be low, Kupffer cells alone do not proliferate. Accordingly, even if Kupffer cell clones can be obtained by this method, it is still difficult to efficiently produce a large amount of Kupffer cells in a convenient way.

CITATION LIST

Patent Literature

[PTL 1] International Publication No. WO2002/059279

Non Patent Literature

[NPL 1] G. Heuff et al. (1994) J. Immunol. Methods 14: 61-65

[NPL 2] J. K. Olynyk et al. (1998) J. Gastroenterol. Hepatol. 13: 842-845

[NPL 3] V. Valatas et al. (2003) Cell Biol. Int. 27: 67-73

[NPL 4] Experimental Manual for Macrophage, Kodansha Scientific Ltd. (1992) 28-35

[NPL 5] A. Suzumura et al. (1987) J. Neuroimmunol. 15, 263-278

[NPL 6] Experimental Medicine Separate Volume, Biomanual UP Series, Brain-Nerve Research Protocol, Chapter 1, Culture Techniques for Nervous Tissues, (1) Culturing of Microglia, 1995, Yodosha Company Limited

[NPL 7] Bartlett, P. F. et al. (1988) PNAS 85: 3255-3259

[NPL 8] Takenouchi, T. et al. (2005) Biochim. Biophys. Acta 1726: 177-186

[NPL 9] Froh M. et al. (2003) Gastroenterology 124: 172-183

[NPL 10] Handa Hiroshi, LANDFALL, Vol. 42, pp. 1-6, April 2001

[NPL 11] Handa Hiroshi, Acta Obstetrica et Gynaecologica Japonica, Vol. 56, No. 9, N-498 to 502, 2004

SUMMARY OF INVENTION

Technical Problem

The present invention has been made in consideration of the above-described problems in the conventional techniques. An object of the present invention is to provide a method capable of efficiently producing a large amount of Kupffer cells in a convenient way.

Solution to Problem

The present inventors performed a primary culture of a fraction mainly composed of hepatic parenchymal cells (hereinafter referred to as a "hepatic parenchymal cell fraction") obtained by centrifuging cells derived from the liver of a mammal such as rat, mouse, and cattle. The culture was continued even after the hepatic parenchymal cells became absent substantially as a result of the death or morphological change. Unexpectedly, the followings were subsequently found out for the first time in the world. Specifically, fibroblast-like cells proliferated and formed a cell layer. Kupffer cells then appeared on the cell layer and actively proliferated. Kupffer cells do not proliferate when cultured in a normal medium. In contrast, the Kupffer cells presumably proliferated in the primary culture as follows. Specifically, the fibroblast-like cell layer appeared after the hepatic parenchymal cells became absent substantially; then, the fibroblast-like cell layer stimulated the activity of a small number of Kupffer cells contained in the hepatic parenchymal cell fraction prior to the primary culture; thus, the Kupffer cells actively proliferated. Further, the Kupffer cells proliferated in the primary culture were satisfactorily and conveniently collected by shaking the culturing vessel for the primary culture to thereby dissociate the Kupffer cells in the culture solution. Moreover, by collecting Kupffer cells selected on the basis of the adherence of the Kupffer cells thus collected to a plastic container, the purity of the Kupffer cell was satisfactorily further increased.

There are cases in which cells floated into a culture solution are selected on the basis of the adherence to the plastic container when microglial cells constituting the central nervous system are prepared (Non Patent Literatures 5, 6). Nonetheless, the cell type is different from that in the present invention. Note that a method is known in which Kupffer cells are separated from cells derived from a liver on the basis of the adherence to a plastic container (Non Patent Literature 4). In the method, a mixture of liver cells treated with a collagenase solution is filtered through gauze, and then Kupffer cells are separated from a supernatant obtained by a low-speed centrifugation operation (550 rpm). Meanwhile, the present invention is a method in which: a supernatant obtained by a low-speed centrifugation operation (for example, a centrifugal force of 50×g (approximately 550 rpm when converted to the revolution per minute)) from a mixture of liver cells treated with a collagenase solution is removed, a hepatic parenchymal cell fraction that is a precipitate is cultured, and cells floated into a culture solution are selected and collected on the basis of the adherence to a plastic container. Such a method for producing a Kupffer cell has not been performed at all until the present invention is completed.

As described above, the present inventors have successfully established for the first time in the world a mixed culture system capable of proliferating a Kupffer cell in a primary culture of a cell population derived from a liver. Additionally, using this mixed culture system of the present invention, an efficient production method for Kupffer cells which have been difficult to produce conveniently in a large amount was successfully established.

The use of the mixed culture system established by the present inventors makes it possible to identify a compound influencing proliferation of a Kupffer cell and a compound influencing a biological activity of a Kupffer cell. Moreover, immortalization of the Kupffer cell thus produced makes it possible to stably maintain the Kupffer cell. Further, the Kupffer cell produced by the method of the present invention is usable also as a carrier of a DDS preparation for delivering a desired drug to the liver.

Specifically, the present invention relates to a proliferation method for a Kupffer cell in a mixed culture system, a method for producing a Kupffer cell using the proliferation method, a screening method for a compound influencing proliferation of a Kupffer cell and a screening method for a compound influencing a biological activity of a Kupffer cell, as well as the use of a Kupffer cell produced by the production method. More specifically, the present invention provides the followings.

(1) A proliferation method for a Kupffer cell, characterized by comprising performing a primary culture of a cell population comprising at least a hepatic parenchymal cell and a Kupffer cell derived from a mammalian liver.

(2) The proliferation method according to (1), wherein the cell population is a hepatic parenchymal cell fraction.

(3) The proliferation method according to any one of (1) and (2), wherein the primary culture is continued even after the hepatic parenchymal cell becomes absent substantially.

(4) The proliferation method according to any one of (1) to (3), wherein the primary culture is performed for 5 days or longer.

(5) The proliferation method according to any one of (1) to (4), wherein the primary culture is performed for any period until the proliferation of the Kupffer cell ceases.

(6) The proliferation method according to any one of (1) to (5), wherein in a case where a culturing vessel performing the primary culture is shaken, Kupffer cells dissociated into a culture solution by the shaking are collected, and Kupffer cells adherent to a plastic container are selected and collected from the collected Kupffer cells, the primary culture is performed until the Kupffer cells thus collected have a purity of 90% or higher.

(7) A method for evaluating whether or not a test compound influences proliferation of a Kupffer cell, comprising the steps of:

(a) performing the proliferation method according to any one of (1) to (6) under a condition where a test compound is present in a culture solution; and (b) detecting the proliferation of the Kupffer cell.

(8) A method for producing a Kupffer cell, comprising the steps of:

(a) performing the proliferation method according to any one of (1) to (6); and (b) collecting Kupffer cells thus proliferated.

(9) The method for producing a Kupffer cell according to (8), wherein the step (b) of collecting the Kupffer cells is performed by:

shaking the culturing vessel performing the primary culture; and collecting Kupffer cells dissociated into a culture solution by the shaking.

(10) The method for producing a Kupffer cell according to any one of (8) and (9), further comprising a step of selecting and collecting cells adherent to a plastic container from the collected Kupffer cells.

(11) The method for producing a Kupffer cell according to any one of (8) to (10), wherein after the Kupffer cell is proliferated, the Kupffer cells are collected.

(12) The method for producing a Kupffer cell according to any one of (8) to (11), wherein the Kupffer cells are collected at day 5 or later after the primary culture is started.

(13) The method for producing a Kupffer cell according to any one of (8) to (12), wherein the Kupffer cells are collected after the Kupffer cell proliferates until the proliferation of the Kupffer cell ceases, or after the proliferation of the Kupffer cell ceases.

(14) The method for producing a Kupffer cell according to any one of (8) to (13), wherein the Kupffer cells are collected between day 5 and day 20 after the primary culture is started.

(15) A method for producing an immortalized Kupffer cell, comprising the steps of:

(a) producing a Kupffer cell by the method according to any one of (8) to (14); and (b) performing an immortalization treatment on the produced Kupffer cell.

(16) A method for evaluating whether or not a test compound influences a biological activity of a Kupffer cell, comprising the steps of:
(a) producing a Kupffer cell by the method according to any one of (8) to (15);
(b) bringing a test compound into contact with the produced Kupffer cell; and
(c) detecting a biological activity of the Kupffer cell.
(17) A method for producing a DDS preparation for delivering a desired drug to a liver, comprising the steps of:
(a) producing a Kupffer cell by the method according to any one of (8) to (15); and
(b) causing the produced Kupffer cell to possess a drug desired to be delivered to a liver.

Advantageous Effects of Invention

According to the present invention, an efficient proliferation method has been completed for a Kupffer cell using a mixed culture system of cells derived from a liver. The use of the proliferation method for a Kupffer cell of the present invention makes it possible to proliferate a Kupffer cell in the mixed culture system of cells derived from a liver, and to collect the Kupffer cells. Besides, the Kupffer cells can be collected from the mixed culture system repeatedly multiple times during the primary culture. Moreover, the Kupffer cells can be collected from the mixed culture system through separation by shaking a culturing vessel for the cultured cell mixture. Further, by the selection and collection based on the strong adherence to a plastic container, the purity of the Kupffer cells thus collected can be further increased.

Conventionally, specific cells derived from a liver have been produced from a mixture population of dispersed liver cells by making use of various fractionation•purification processes from the viewpoint of how high-purity target cells are collected. This approach is not suitable for mass production of Kupffer cells. Meanwhile, the method of the present invention makes it possible to produce a large amount of high-purity Kupffer cells conveniently using only conventional experimental equipment without requiring skilled techniques.

Specifically, the method of the present invention makes it possible to continuously select and collect Kupffer cells from a single tissue culture flask every 2 to 3 days for approximately 2 weeks on the basis of the adherence to a plastic container. As a result, when a tissue culture flask having a bottom area of 75 $cm^2$ is used, approximately $1\times10^7$ Kupffer cells can be collected per tissue culture flask (approximately $1\times10^6$ to approximately $3\times10^6$ by one-time collection). A total number of cells that can be collected is proportional to the bottom area and the number of tissue culture flasks. Hence, when all of the liver cells obtained from, for example, a single rat individual are used, the cells can be cultured using approximately 50 tissue culture flasks (each having a bottom area of 75 $cm^2$); eventually, approximately $5\times10^8$ Kupffer cells can be collected. This value is 50 to 100 times as large as the number of Kupffer cells obtained from a single rat individual by conventional methods (methods in which a Kupffer cell fraction is harvested on the basis of the cell density: Non Patent Literatures 1 to 3). Thus, the method of the present invention is quite suitable for mass production of Kupffer cells in comparison with the conventional methods.

Furthermore, the collected Kupffer cells can be cryopreserved using a conventional cell freezing medium. These frozen Kupffer cells can be stably kept in liquid nitrogen for an extended period (at least 2 years), and can be thawed for use as necessary.

By introduction or the like of an oncogene into the Kupffer cell produced according to the method of the present invention, it is possible to obtain an immortalized cell line capable of permanent subculturing while retaining the cytological properties of the Kupffer cell. Moreover, a Kupffer cell thus produced is usable, for example, as a carrier of a DDS preparation for delivering a desired drug such as an anti-cancer agent to a liver, or as a tool for evaluating whether or not a test compound influences a biological activity of the Kupffer cell.

The use of the mixed culture system for proliferating a Kupffer cell established in the present invention makes it possible to evaluate whether or not a test compound influences proliferation of the Kupffer cell.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 5 shows (A) fluorescence microphotographs and (B) graphs of FACS analysis, showing the result of detecting incorporation (phagocytosis) of FITC fluorescent dye-labeled latex beads by Kupffer cells (21 days after the primary culture was started) selected and collected on the basis of the adherence to the plastic dish. The cells were derived from the rats.

Figure 15:
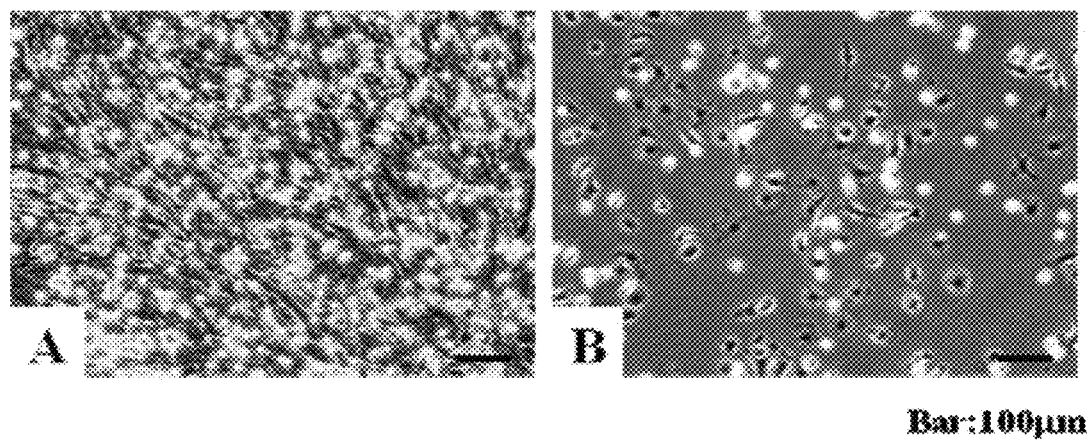

A in FIG. 15 is a phase-contrast microphotograph of a mixed culture system (13 days after the primary culture was started) into which a human oncogene c-myc was introduced. B in FIG. 15 is a phase-contrast microphotograph of Kupffer cells (13 days after the primary culture was started) selected and collected on the basis of the adherence to a plastic dish. The cells were derived from the mice. The scale bar represents 100 μm.

Figure 16:
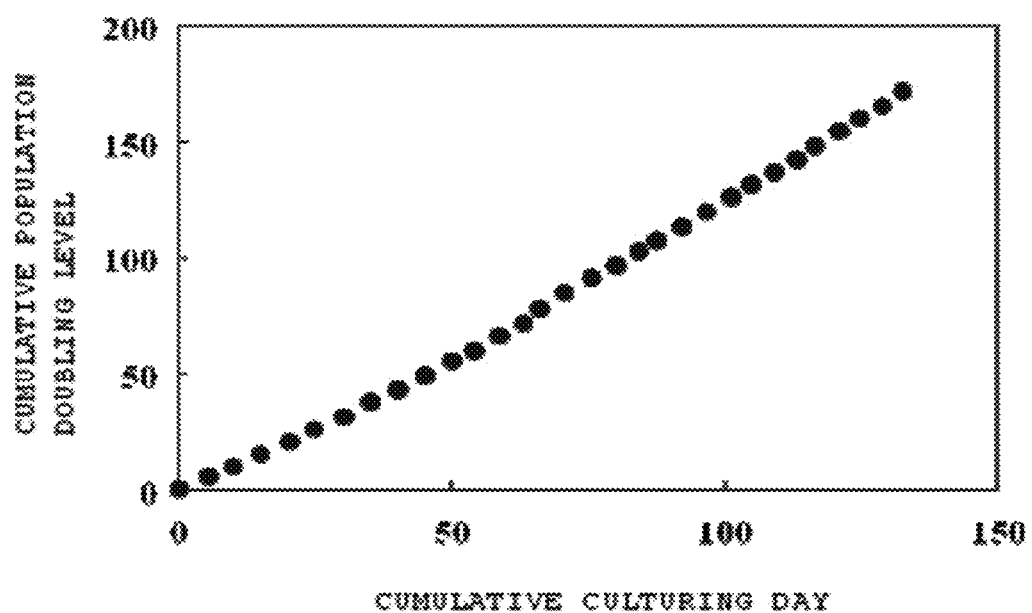

FIG. 16 is a graph showing the proliferation trend of Kupffer cells immortalized by introduction of the human oncogene c-myc. The cells were derived from the mice.

Figure 17:
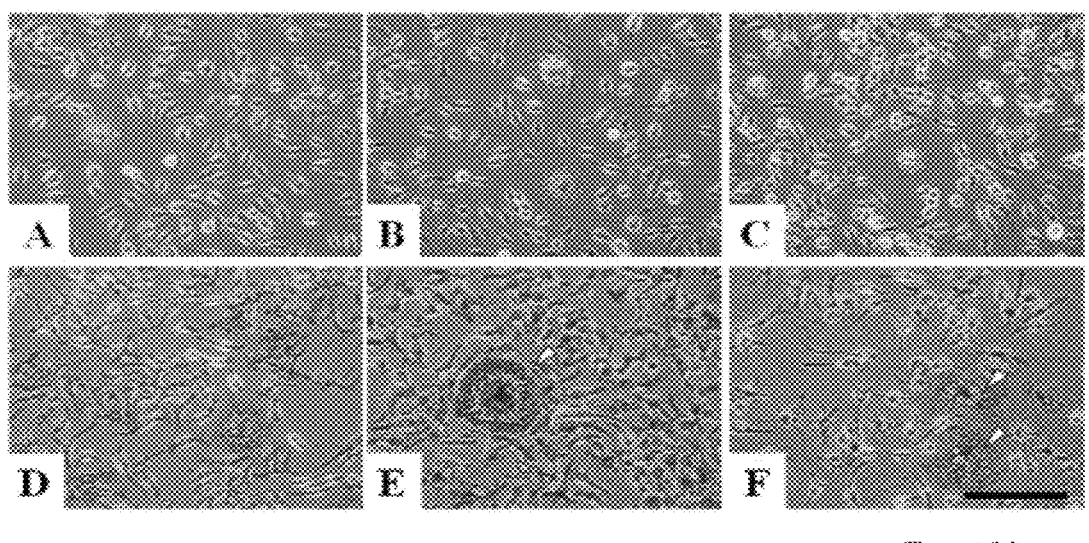

FIG. 17 shows microphotographs showing the result of immunostaining the Kupffer cells selected and collected on the basis of the adherence to the plastic dish. The cells were derived from the mice. A shows that with cytokeratin 18; B with cytokeratin 19; C with SMA; D with Mac-1; E with F4/80; and F with KT022. The arrowheads in E and F indicate cells formed into multinucleated cells by cell fusion. The scale bar represents 100 μm.

DESCRIPTION OF EMBODIMENTS

<Proliferation Method for Kupffer Cell>

The present invention is based on the knowledge obtained by the present inventors that a mixed culture system for efficiently proliferating a Kupffer cell can be established by performing a primary culture of a cell population comprising a hepatic parenchymal cell and a Kupffer cell derived from a mammalian liver. Accordingly, the present invention provides an efficient proliferation method for a Kupffer cell, characterized by comprising performing a primary culture of a cell population comprising at least a hepatic parenchymal cell and a Kupffer cell derived from a mammalian liver.

In the present invention, the "hepatic parenchymal cell" means a cell constituting a liver and substantially playing the liver function. The "hepatic non-parenchymal cell" means a cell constituting the liver other than the hepatic parenchymal cell. The "Kupffer cell" means one of non-parenchymal cells constituting the liver, and is one type of macrophages. The term "primary culture" means culturing of a dissociated cell from a living organism until the first passaging. The "mixed culture system" means a culture system in such a state that a fibroblast-like cell is formed by primary culture of a cell population comprising a hepatic parenchymal cell and a Kupffer cell of a mammal. The "culturing vessel" should be a commonly-used tissue culturing vessel capable of culturing a cell; if so, the material and shape thereof are not particularly limited. For example, a tissue culture flask made of glass, a tissue culture flask made of plastic, or the like is suitably used. Moreover, the "plastic container" should be a commonly-used plastic container capable of culturing a cell; if so, the type and shape of the plastic are not particularly limited. For example, a polyethylene plastic dish, a polystyrene plastic dish, or the like is used. Preferably, a bacteria-culture plastic dish or a non-surface-treated plastic dish (non-coated plastic dish) is used.

In the present invention, the "cell population comprising at least a hepatic parenchymal cell and a Kupffer cell derived from a liver" is not particularly limited, as long as a mixed culture system for the Kupffer cell can be established by primary culture. The cell population may be a hepatic parenchymal cell fraction or a hepatic non-parenchymal cell fraction derived from the mammalian liver, but is preferably a hepatic parenchymal cell fraction. Herein, the "hepatic parenchymal cell fraction" is a fraction of cells derived from the liver, which contains a larger number of hepatic parenchymal cells than hepatic non-parenchymal cells. The "hepatic non-parenchymal cell fraction" is a fraction containing a larger number of hepatic non-parenchymal cells than hepatic parenchymal cells. The hepatic parenchymal cell fraction is generally a cell fraction obtained as a precipitate by a low-speed centrifugation operation from liver cells obtained by a collagenase perfusion method. In the low-speed centrifugation operation to obtain a hepatic parenchymal cell fraction, the centrifugal force is 10 to 600×g, preferably 30 to 60×g; and the centrifugation period is 1 to 15 minutes, preferably 1 to 5 minutes. The centrifugation operation is normally performed at a temperature in such a range as not to damage the cells, for example, 0 to 25° C., preferably 4 to 15° C., and further preferably 4 to 10° C. Such centrifugation operations and a washing operation with a medium are repeated 1 to 5 times, preferably 2 to 3 times, and thereby the hepatic parenchymal cell fraction can be obtained. Examples of the mammal from which the cell population is derived include rat, mouse, cattle, horse, sheep, monkey, human, and the like, but are not limited thereto.

Moreover, in the present invention, the phrase "the hepatic parenchymal cell becomes absent substantially" means that most (for example, 90% or more, 95% or more, 98% or more, 99% or more) of the hepatic parenchymal cell before the primary culture are no longer present in the mixed culture system after the primary culture.

In the present invention, when the primary culture of the hepatic parenchymal cell fraction is performed for an extended period, this allows proliferation of the Kupffer cell comprised in the hepatic parenchymal cell fraction. Surprisingly, the present inventors have found out the following facts. Specifically, when the primary culture of the hepatic parenchymal cell fraction is continued even after the hepatic parenchymal cell becomes absent substantially as a result of the death or morphological change, a fibroblast-like cell layer spreads in the mixed culture system. Subsequently, because of the supporting effect by the fibroblast-like cell layer, the Kupffer cell actively proliferates on this layer. Thus, a preferable embodiment of the proliferation method for a Kupffer cell of the present invention is that the primary culture is continued even after the hepatic parenchymal cell becomes absent substantially.

In the mixed culture system in the primary culture, the Kupffer cells are mainly pre sent on and loosely adhering to the fibroblast-like cell layer. Accordingly, when the culturing vessel performing the primary culture is shaken, the Kupffer cells are dissociated into the culture solution by the shaking. In addition, Kupffer cells have a very strong adherence to a plastic container. Accordingly, when the collected Kupffer cells are cultured in a plastic container and Kupffer cells adherent to the plastic container are selected and collected, the purity of the Kupffer cells can be further increased. Thus, in the proliferation method for a Kupffer cell of the present invention, in a case where a culturing vessel performing the primary culture is shaken, Kupffer cells dissociated into a culture solution by the shaking are collected, and Kupffer cells adherent to a plastic container are selected and collected from the collected Kupffer cells, a preferable culturing period is when the Kupffer cells thus selected have a high purity (for example, a purity of 90% or higher, 95% or higher, 98% or higher, 99% or higher). The shaking operation and the operation of selecting the Kupffer cells adherent to the plastic container will be described in detail in the section of "Method for Producing Kupffer Cell" to be described later.

The purity of the Kupffer cells collected by the shaking and that of the Kupffer cells adhering to the plastic container and thus selected and collected can be evaluated, for example, by the ratio of cells stained with a specific antibody after immunostaining described in Example 1.

The culturing period of the primary culture is selected as appropriate, depending on the animal from which the cells used as the origin. For example, the primary culture can be performed for any period until the proliferation of the Kupffer cell ceases. The primary culture may be continued even after the proliferation of the Kupffer cell ceases. The culturing period is, for example, at least 5 days or longer, preferably 1 week or longer (for example, 10 days or longer, 2 weeks or longer). The culturing for an extended period can increase the chance of collecting Kupffer cells. Nevertheless, when the culturing is performed for an extended period, the proliferation of the Kupffer cell is decreased, and the amount of the Kupffer cells collected is decreased. Hence, the culturing period of the primary culture is preferably 5 to 40 days, particularly preferably 5 to 30 days.

In the proliferation method of the present invention, a medium used for the primary culture is not particularly limited, as long as the mixed culture system for proliferating the Kupffer cell can be established. The medium used in Examples of the present invention is Dulbecco's modified Eagle's medium (high glucose type) supplemented with fetal bovine serum (10%), bovine insulin (10 μg/ml), and 2-mercaptoethanol (0.1 mM). Alternatively, other media are also usable.

<Method for Evaluating Whether or Not Test Compound Influences Proliferation of Kupffer Cell>

Using the proliferation method for a Kupffer cell of the present invention in the presence of a test compound, whether or not the test compound influences proliferation of a Kupffer cell can be evaluated. Thus, the present invention provides a method for evaluating whether or not a test compound influences proliferation of a Kupffer cell, comprising the steps of:

performing the proliferation method for a Kupffer cell of the present invention under a condition where a test compound is present in a culture solution; and detecting the proliferation of the Kupffer cell.

Herein, the phrase "influences proliferation" is meant to include both cases where the test compound promote s and inhibits the proliferation of the Kupffer cell.

The test compound is not particularly limited, and a desired compound subjected to the evaluation as to whether or not to influence the proliferation of the Kupffer cell can be used. Examples of the test compound include purified or partially purified proteins, peptide compounds, low-molecular-weight synthetic compounds, natural compounds, cell extracts, cell culture supernatants, microbial products, marine organism extracts, plant extracts, and the like, but are not limited thereto. The test compound can be brought into contact with the Kupffer cell by, for example, adding the test compound to a medium in which the Kupffer cell is cultured. The proliferation of the Kupffer cell can be detected by, for example, calculating the number of Kupffer cells in the mixed culture system after immunostaining described in Example 1. As a result, if the number of Kupffer cells is increased in comparison with a case where the detection is performed in the absence of the test compound, the test compound is evaluated as having an activity of promoting the proliferation of the Kupffer cell. Meanwhile, if the number of Kupffer cells is decreased in comparison with a case where the detection is performed in the absence of the test compound, the test compound is evaluated as having an activity of inhibiting the proliferation of the Kupffer cell.

By selecting a compound influencing the proliferation of the Kupffer cell from multiple test compounds evaluated as described above, it is possible to screen for: drugs modulating the proliferation of the Kupffer cell; drug candidate compounds against diseases (for example, liver dysfunction, hepatitis, cirrhosis, and the like) associated with a Kupffer cell; and so on.

<Method for Producing Kupffer Cell>

Further, the present invention provides a method for efficiently producing a Kupffer cell using the proliferation method for a Kupffer cell of the present invention. Thus, the method for producing a Kupffer cell of the present invention comprises the steps of:

performing the proliferation method of the present invention; and collecting Kupffer cells thus proliferated.

Figure 1:
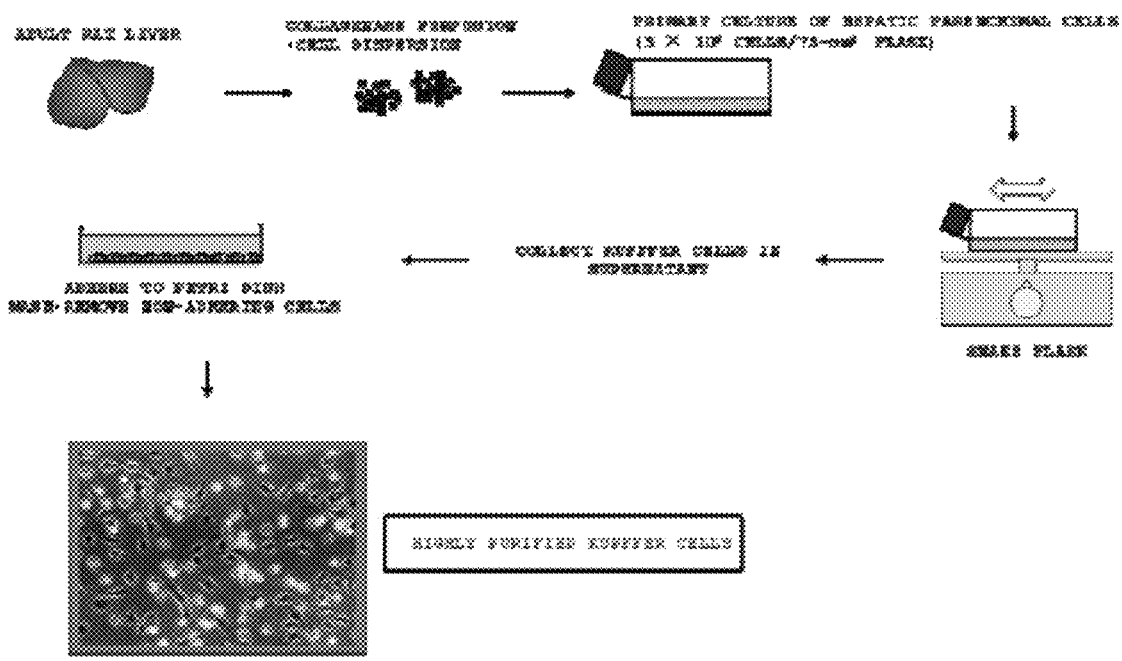
FIG. 1 shows a diagram for illustrating one embodiment of a method for producing a Kupffer cell of the present invention using a T-75 tissue culture flask (bottom area: 75 $cm^2$) and a Petri dish (one type of a plastic dish).

The method for collecting the Kupffer cells proliferated in the primary culture is not particularly limited. Nevertheless, from the point that high-purity Kupffer cells can be collected conveniently, a preferable method comprises:

shaking the culturing vessel performing the primary culture; and collecting Kupffer cells dissociated into a culture solution by the shaking. The shaking operation can be performed, for example, in the mode of reciprocal shaking at 60 to 180 rpm, preferably 80 to 120 rpm, for 10 to 120 minutes, preferably 30 to 60 minutes. By selecting and collecting Kupffer cells adherent to a plastic container from the collected Kupffer cells, the purity of the Kupffer cells can be further increased (FIG. 1). For example, the collected Kupffer cells are seeded into a plastic container and incubated for 10 to 60 minutes, preferably 20 to 30 minutes. Then, cells non-adherent to a plastic container are removed by washing with a saline or the like. Thereby, the Kupffer cells adherent to the plastic container can be selected and collected. The method of the present invention makes it possible to efficiently produce a large amount of Kupffer cells having a purity of 90% or higher (for example, 95% or higher, 98% or higher, 99% or higher).

The Kupffer cells may be collected from the primary culture without any particular limitation, as long as the cells are collected after the Kupffer cell proliferates on a fibroblast-like cell layer. For example, the Kupffer cells may be collected in any time until the proliferation of the Kupffer cell ceases, or for any period after the proliferation of the Kupffer cell ceases. For example, a suitable collecting period is selected as appropriate, depending on the type of the mammal. From the point that a large amount of Kupffer cells can be collected, the Kupffer cells are preferably collected at day 5 or later after the primary culture is started, and the Kupffer cells are further preferably collected between day 5 and day 40. In a case of rats or mice, the Kupffer cells are particularly preferably collected between day 5 and day 20 after the primary culture is started, and further preferably collected between day 7 and day 14 after the primary culture is started. In a case of cattle, the Kupffer cells are particularly preferably collected between day 10 and day 35 after the primary culture is started, and further preferably collected between day 15 and day 30 after the primary culture is started.

<Methods for Cryopreserving and Thawing Kupffer Cells>

Kupffer cells (for example, at a density of approximately $3 \times 10^6$/ml) collected by the method for producing a Kupffer cell of the present invention are suspended in a cell-cryopreservation solution, and then dispensed into a freezing vial, followed by freezing in a freezer (for example, –80° C.). Next, after transferred into liquid nitrogen, the Kupffer cells can be cryopreserved for an extended period (for example, approximately 2 years). For thawing, the vial is immersed in warm water (for example, 37° C.) and rapidly thawed. Thus, the Kupffer cell can be used in the same state as that before the cryopreservation.

Note that after a portion of the cell suspension is taken and mixed with an equivalent amount of trypan blue staining solution, a cell-collecting ratio and a ratio of live cells per vial can be calculated by counting live cells (not stained with trypan blue) and dead cells (stained blue) using a hemocytometer.

<Method for Producing Immortalized Kupffer Cell>

Kupffer cells thus produced can continuously proliferate by performing an immortalization treatment. Thus, the present invention provides a method for producing an immortalized Kupffer cell, comprising the steps of:

producing a Kupffer cell by the method for producing a Kupffer cell of the present invention; and performing an immortalization treatment on the produced Kupffer cell.

In the present invention, the immortalization treatment is not particularly limited. An example thereof is introduction of an oncogene. By introducing an oncogene into the Kupffer cell, an immortalized cell line capable of permanent subculturing while retaining the properties of the Kupffer cell can be obtained.

One example of specific techniques is as follows. Specifically, in the same manner as in the proliferation method for a Kupffer cell of the present invention, first, a primary culture of a hepatic parenchymal cell fraction derived from the mammalian liver is performed. When Kupffer cells start actively proliferating, the Kupffer cells are infected with a retrovirus vector containing a human oncogene c-myc and a neomycin resistance gene in the same manner as in the cell immortalization method described in the known documents (Non Patent Literatures 7, 8). Then, Kupffer cells dissociated into a culture solution by shaking the culturing vessel are collected. Cells adherent to a plastic container are selected from the collected Kupffer cells, and cultured in a medium supplemented with an antibiotic (neomycin). Thereby, a Kupffer cell into which the human oncogene c-myc is introduced is selectively allowed to proliferate. A cloning operation is performed on this cell by a commonly-used method. Thus, an immortalized high-purity Kupffer cell line can be obtained. In a case of using a retrovirus vector, a Kupffer cell derived from a mouse liver is preferably used from the point of high susceptibility to infection with the vector.

<Method for Evaluating Whether or Not Test Compound Influences Biological Activity of Kupffer Cell>

The use of a Kupffer cell produced by the method for producing a Kupffer cell of the present invention makes it possible to evaluate whether or not a test compound influences a biological activity of the Kupffer cell. Thus, the present invention provides a method for evaluating whether or not a test compound influences a biological activity of a Kupffer cell, comprising the steps of:

producing a Kupffer cell by the method for producing a Kupffer cell of the present invention;

bringing a test compound into contact with the produced Kupffer cell; and detecting a biological activity of the Kupffer cell.

Herein, the phrase "influence a biological activity" is meant to include both cases where the test compound promotes and inhibits the biological activity of the Kupffer cell.

The test compound is not particularly limited, and a desired compound subjected to the evaluation as to whether or not to influence the biological activity of the Kupffer cell can be used. Examples of the test compound include purified or partially purified proteins, peptide compounds, low-molecular-weight synthetic compounds, natural compounds, cell extracts, cell culture supernatants, microbial products, marine organism extracts, plant extracts, and the like, but are not limited thereto.

The test compound can be brought into contact with the Kupffer cell by, for example, adding the test compound to a medium in which the Kupffer cell is cultured. Moreover, the biological activity of the Kupffer cell can be detected, for example, as in Example 1 of the present invention on the basis of: the ability to phagocytose fluorescent dye-labeled latex beads; the proliferative response to cytokine; and the productivity of an inflammatory cytokine upon stimulation with a lipopolysaccharide (LPS). As a result, if the Kupffer cell is detected to have a high biological activity in comparison with the biological activity of a Kupffer cell not brought into contact with the test compound, the test compound is evaluated as having a high activity of promoting the biological activity of the Kupffer cell. Meanwhile, if the Kupffer cell is detected to have a low biological activity in comparison with the biological activity of a Kupffer cell not brought into contact with the test compound, the test compound is evaluated as having an activity of inhibiting the biological activity of the Kupffer cell.

By selecting a compound influencing the biological activity of the Kupffer cell from multiple test compounds evaluated as described above, it is possible to screen for: drugs modulating the biological activity of the Kupffer cell; and drug candidate compounds against diseases (liver dysfunction, hepatitis, cirrhosis, and the like) associated with a Kupffer cell.

<Method for Producing DDS Preparation for Delivering Desired Drug to Liver>

Additionally, researches and developments have been actively carried out all over the world on a drug delivery system (DDS), as one of drug therapies, for delivery to a required site at a required timing of a required drug possessed by a transporter (carrier). Since a Kupffer cell has been known to move to a liver tissue (Non Patent Literature 9), a Kupffer cell produced by the method of the present invention can be used for production of a DDS preparation for delivering a desired drug to a liver. Thus, the present invention provides a method for producing a DDS preparation for delivering a desired drug to a liver, comprising the steps of:

producing a Kupffer cell as a carrier of a DDS preparation by the method for producing a Kupffer cell of the present invention; and causing the produced Kupffer cell to possess a drug desired to be delivered to a liver.

The drug to be delivered to the liver is not particularly limited. Examples thereof include drugs for treating or preventing a disease associated with a liver (for example, anti-cancer compounds for treating liver cancer, anti-inflammatory compounds for treating hepatitis). Moreover, as an example of the method for causing the Kupffer cell to possess the desired drug to be delivered to the liver, one includes: coupling the drug to latex beads by a commonly-used method; and allowing Kupffer cells to phagocytose the drug-coupled latex beads thus obtained.

For example, latex beads coupled to an anti-cancer compound are phagocytosed by Kupffer cells, which are then intravenously administered to a mammal having liver cancer. Thereby, the administered Kupffer cells move to the liver through the blood circulation in the body, and incorporated into the liver that is a source tissue of Kupffer cells, then releasing the anti-cancer compound. In this manner, the liver cancer cells can be killed. The latex beads are not particularly limited. For example, commonly-used latex beads capable of being coupled to a drug or a DNA can be used. It is possible to suitably use latex beads produced by adding divinyl benzene as a crosslinking agent to a copolymer of styrene and glycidyl methacrylate (GMA), to the surface of which GMA is further coupled (Non Patent Literatures 10, 11). The anti-cancer compound can be coupled to the latex beads, for example, by employing a commonly-used method to react the latex beads with the anti-cancer compound having, in a spacer, a functional group (for example, an amino group) capable of being coupled to an epoxy group of GMA of the latex beads. As the spacer for coupling the anti-cancer compound to the latex beads, the same spacer (for example, a polypeptide consisting of several amino acids, or the like) as used for commonly-used DDS preparations can be used. Preferably, a spacer capable of releasing an anti-cancer compound in a liver tissue can be used without any particular limitation. For example, a spacer having a peptide bond or an ester bond specifically cut out by an enzyme existing in a liver is particularly preferable. The length of the spacer, the size of the latex beads, the amount of the anti-cancer compound coupled to the latex beads, the amount of the latex beads coupled to the anti-cancer compound phagocytosed by a Kupffer cell, the amount of the administered Kupffer cells phagocytosing the latex beads coupled to the anti-cancer compound, and so on are selected as appropriate through observation of the therapeutic effect on liver cancer of mammals. Similarly, the use of latex beads coupled to an anti-inflammatory compound enables treatment of hepatitis in mammals.

Additionally, the use for screening for drug candidate compounds is possible by verifying the therapeutic effect and prevention effect of drug candidate compounds against liver cancer and hepatitis, the drug candidate compound being possessed by the Kupffer cell administered to model animals for liver cancer and hepatitis.

EXAMPLES

Hereinafter, the present invention will be more specifically described based on Examples and Comparative Example. However, the present invention is not to be limited to Examples below.

Example 1

Production of Kupffer Cells from Rat Liver

In the same manner as in the method described in the known document (Non Patent Literature 4), the livers of adult male SD rats (10 to 15 weeks old) were perfused with a collagenase solution, and digested liver tissues were removed.

Figure 2:
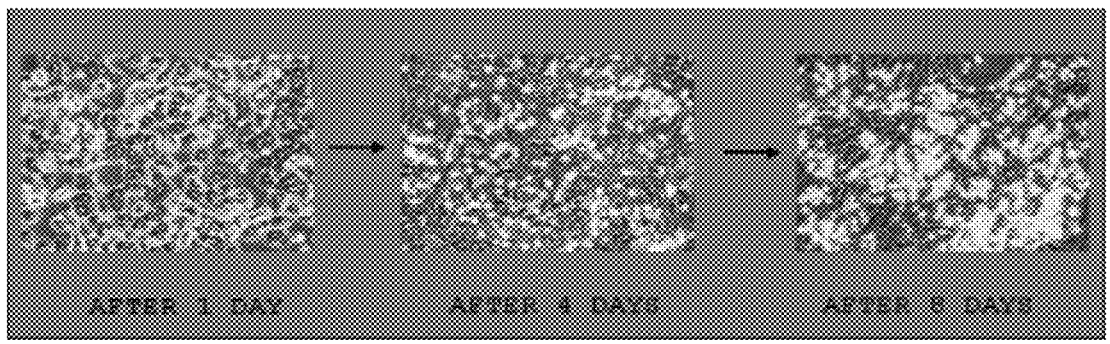
FIG. 2 shows phase-contrast microphotographs of a primary culture of hepatic parenchymal cells (1 day, 4 days, and 8 days after the primary culture was started). The cells were derived from rats.

Each of the removed liver tissues was minced. To this, a collagenase solution was added, and a liver cell mixture suspension was obtained by pipetting. A low-speed centrifugation operation (50×g for 1 minute) at 4° C. and a washing operation with a medium (which is a Dulbecco's modified Eagle's medium (high glucose type) supplemented with fetal bovine serum (10%), bovine insulin (10 µg/ml), and 2-mercaptoethanol (0.1 mM)) (hereinbelow, unless otherwise specifically stated, a medium of the same kind was used) were repeated three times on the obtained mixture suspension. A hepatic parenchymal cell fraction that was a precipitate obtained there from was suspended in a medium, and $5\times10^6$ cells were seeded per a polystyrene tissue culture flask having a bottom area of 75 $cm^2$ (Sumitomo Bakelite Co., Ltd. MS-21250 (250 ml, 75 $cm^2$)) (hereinbelow, unless otherwise specifically stated, a tissue culture flask having the same material and bottom area was used). In this primary culture, the hepatic parenchymal cells became absent substantially at day 5 to week 1. A fibroblast-like cell layer was formed at week 1 to day 10. Spherical macrophage-like cells actively proliferated on the layer. In other words, at week 1 to day 10 after the primary culture was started, a mixed culture system was formed in the tissue culture flask. FIG. 2 shows phase-contrast microphotographs of the cells at 1 day, 4 days, and 8 days after the primary culture was started.

Figure 3:
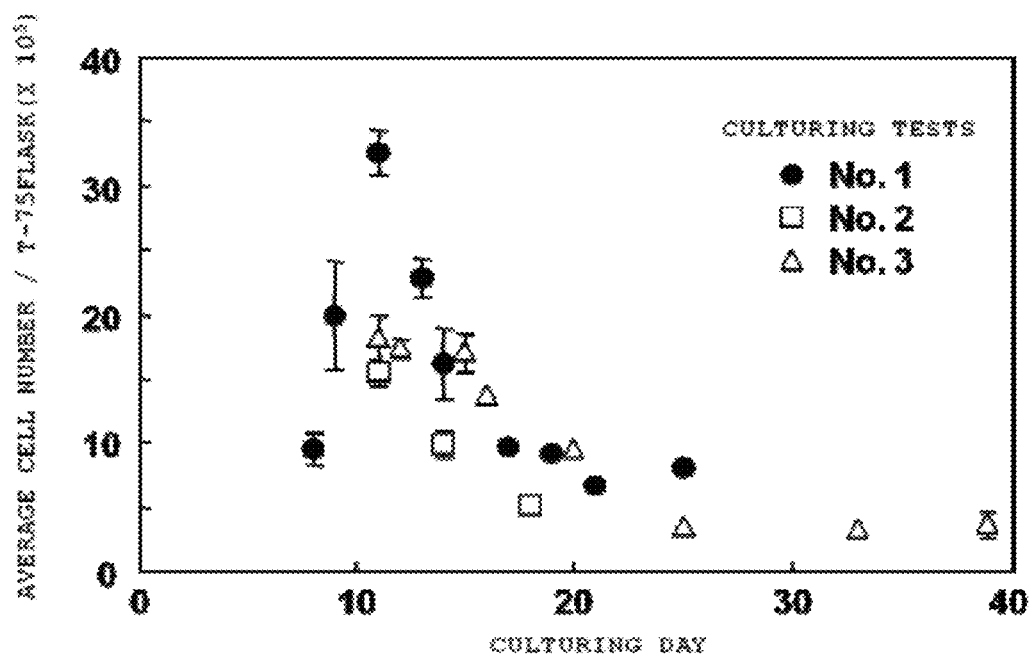
FIG. 3 is a graph showing a relationship between a culturing day and a cell count number of collected Kupffer cells in a mixed culture system using a T-75 tissue culture flask (bottom area: 75 $cm^2$). The cells were derived from the rats.

The tissue culture flasks up to day 40 after the primary culture was started were gently shaken at 37° C. for a short period (reciprocally shaken at 80 to 120 rpm for 30 to 60 minutes), and cells dissociated into the culture solution were collected. Otherwise, the cells dissociated into the culture solution may be precipitated by a centrifugation operation and collected (hereinbelow also, cells dissociated into the culture solution were similarly collected). Alternatively, the culture solution containing the cells dissociated into the culture solution was transferred to a bacteria-culture plastic dish (Non-tissue culture dish: BD Falcon 351005) (hereinbelow, unless otherwise specifically stated, a plastic dish having the same material, size, and shape was used), and incubated for a short period (in a carbon dioxide incubator at 37° C. for 20 to 30 minutes). Cells non-adherent to the plastic dish were removed by washing with Dulbecco's phosphate buffered saline (D-PBS). Cells adhering to the plastic dish were treated with a TrypLE Express solution (manufactured by Invitrogen Corporation), and scraped off from the plastic dish and dissociated into the culture solution. Then, the cells were precipitated by a centrifugation operation and collected (hereinbelow also, cells adhering to the plastic dish were similarly collected) (FIG. 3). A fresh medium was added into the tissue culture flask in which the cells were collected, and the mixed culturing was continued.

Figure 4:
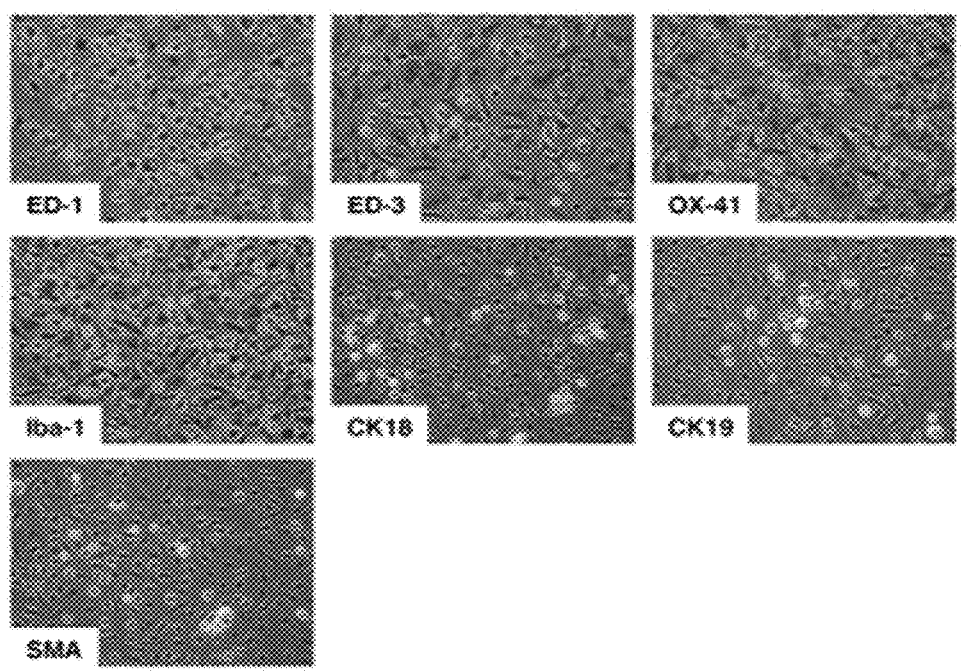
FIG. 4 shows microphotographs showing the result of immunostaining Kupffer cells (12 days after the primary culture was started) selected and collected on the basis of the adherence to a plastic dish. The cells were derived from the rats.

Cells selected and collected on the basis of the adherence to the plastic dish were observed using a phase-contrast microscope, showing quite a similar morphology to that of a macrophage. Further, almost all the cells were strongly stained with rat•macrophage-specific monoclonal antibodies (OX-41, ED-1, ED-3) and anti-Iba-1 rabbit polyclonal antibody (manufactured by Wako Pure Chemical Industries, Ltd.), but not immunostained with anti-cytokeratin 18 (CK18) mouse monoclonal antibody (manufactured by Millipore Corporation), anti-cytokeratin 19 (CK19) mouse monoclonal antibody (manufactured by Progen Biotechnik GmbH) and anti-smooth muscle actin (SMA) mouse monoclonal antibody (manufactured by Progen Biotechnik GmbH) (FIG. 4). From the above result, since cells positive for cytokeratin and smooth muscle actin were hardly found in these cell populations, it was inferred that the collected cells were contaminated with quite a small number of other cell types such as hepatic parenchymal cells and mesenchymal cells (in the judgment by the immunostaining, the contamination ratio of other cell types was 0.1% or less).

Figure 6:
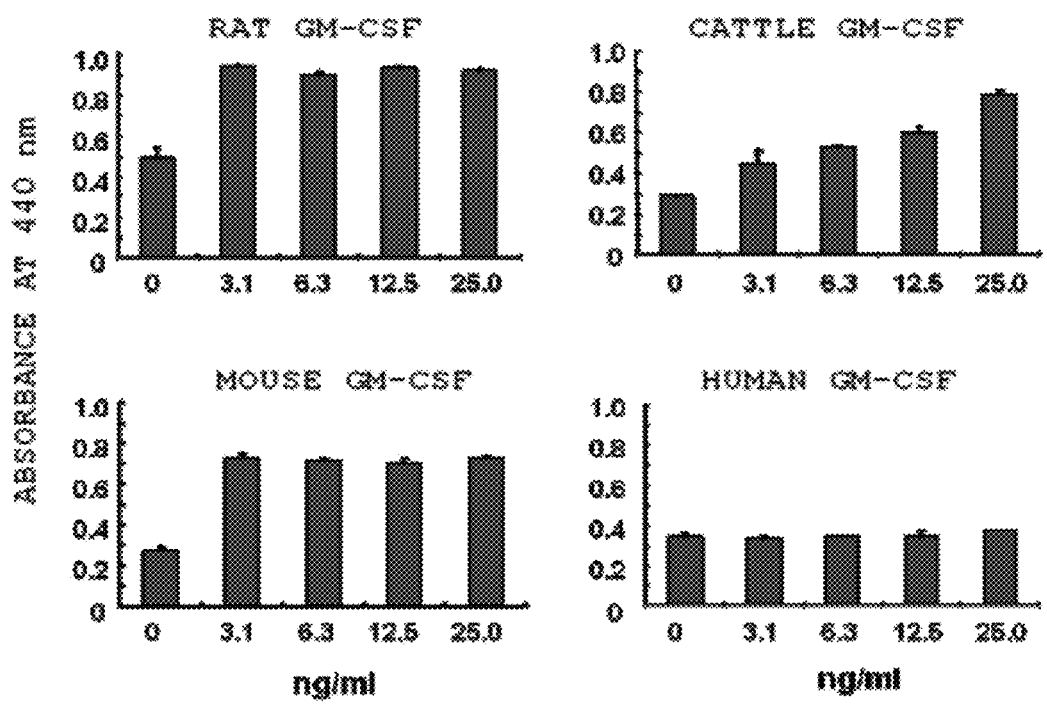
FIG. 6 shows graphs showing the result of detecting the proliferative response to a recombinant cytokine (rat, cattle, mouse, or human-derived rGM-CSF) by Kupffer cells (14 days after the primary culture was started) selected and collected on the basis of the adherence to the plastic dish. The cells were derived from the rats.

Moreover, the cells had biological properties such as an ability to phagocytose FITC fluorescent dye-labeled latex beads (FIG. 5), proliferative response to a recombinant cytokine (rGM-CSF) (FIG. 6), and productivity of an inflammatory or anti-inflammatory cytokine upon stimulation with a lipopolysaccharide (Table 1).

TABLE 1

| Cytokine | Average concentration ± S.E. (pg/ml) |
|---|---|
| IL-6 | 2305 ± 160 |
| IL-12 p40 | 315 ± 74 |
| TNFα | 1639 ± 643 |
| RANTES | 3075 ± 722 |
| IL-10 | 511 ± 67 |

Note that Table 1 shows the result of detecting the productivity of an inflammatory or anti-inflammatory cytokine upon stimulation with a lipopolysaccharide by the cells (14 to 24 days after the primary culture was started) selected and collected on the basis of the adherence to the plastic dish.

Figure 7:
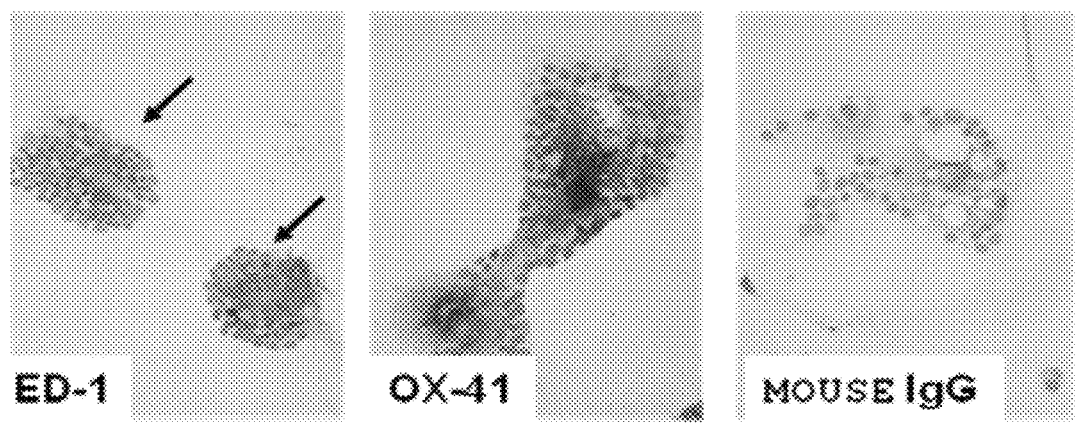
FIG. 7 shows microphotographs showing the formation of fused and multinucleated cells from Kupffer cells (11 days after the primary culture was started) selected and collected on the basis of the adherence to the plastic dish. The cells were derived from the rats.

Furthermore, the collected cells were fused together as the culturing was continued, forming multinucleated giant cells (FIG. 7).

From the above, the cells selected and collected on the basis of the adherence to the plastic dish were revealed to be Kupffer cells. Approximately $1 \times 10^6$ to approximately $3 \times 10^6$ Kupffer cells were collected per tissue culture flask having a bottom area of 75 cm$^2$ by one-time collection (FIG. 3) (a total number of the cells obtained during the entire culturing period was approximately $1 \times 10^7$). From the ratio of the stained cells (Kupffer cells) among the collected cells as a result of the following immunostaining, the purity of the collected Kupffer cells was 98% or higher.

Note that the immunostaining as well as the measurements of the ability to phagocytose FITC fluorescent dye-labeled latex beads, the proliferative response to the recombinant cytokine (rGM-CSF), and the productivity of the inflammatory cytokine upon stimulation with the lipopolysaccharide were performed as follows.

(1) Immunostaining

Using a glass-made 8-well chamber slide (BD Falcon 354118) (hereinbelow, unless otherwise specifically stated, a chamber slide having the same material, size, and shape was used), the cells selected and collected on the basis of the adherence to the plastic dish were washed with a phosphate buffered saline (PBS), and fixed with a fixing solution (95% ethanol+1% acetic acid). The fixing treatment was performed at 4° C. for 15 minutes. After the fixing solution was washed with PBS, a nonspecific binding site of an antibody was masked with a blocking solution (10% normal goat serum+ 1% bovine serum albumin in PBS). The masking treatment was performed at room temperature for 15 minutes. A diluted primary antibody (1:200 to 1:800) was added dropwise to the cells having subjected to the fixing treatment, which was incubated for 1 hour at room temperature. Then, the 8-well chamber slide was washed by a 10-minute PBS treatment. The washing operation was repeated three times. Subsequently, after a reaction with a peroxidase-labeled secondary antibody at room temperature for 1 hour, the 8-well chamber slide was washed by a 10-minute PBS treatment. The washing operation was repeated three times. Next, a DAB color reagent was added dropwise to visualize the site where the primary antibody was bound (site colored dark brown). A specimen was prepared by a commonly-used method for cell observation.

(2) Measurement of Ability to Phagocytose FITC Fluorescent Dye-Labeled Latex Beads Using a glass-made 8-well chamber slide (or plastic dish), FITC fluorescent dye-labeled latex beads (diameter: 1 μm, Polysciences, Inc., Warrington, Pa., diluted into the medium by 1:800) were fed to the cells selected and collected on the basis of the adherence to the plastic dish, followed by culturing at 37° C. for 1 to 4 hours and washing with PBS. The cells were fixed in the same manner as in the above immunostaining. Subsequently, a mounting agent containing a DAPI dye (for nuclear staining) was mounted on the cells for observation with a fluorescence microscope. Further, using a flow cytometer, the incorporation (phagocytosis) of the FITC fluorescent dye-labeled latex beads was quantitatively analyzed.

(3) Measurement of Proliferative Response to Recombinant Cytokine

The cells selected and collected on the basis of the adherence to the plastic dish were seeded into a 96-well tissue culture plate (BD Falcon 353072) by 5000 cells/100 μl/well, and various recombinant cytokines were added thereto each at a final concentration of 3 to 25 ng/ml. After culturing for 4 to 5 days, a cell proliferation assay reagent WST-1 was added to each well by 10 μl/well, and reacted at 37° C. for 2 to 4 hours. Then, the absorbance at 440 nm was measured.

(4) Measurement of Cytokine Productivity upon Stimulation with Lipopolysaccharide (LPS)

The cells selected and collected on the basis of the adherence to the plastic dish were seeded into a plastic dish by $10^6$ cells/60 mm of the dish. The medium was replaced with a medium (approximately 5 ml) supplemented with 10 μg/ml of LPS, which was returned to a carbon dioxide incubator. Approximately 30 hours later, the culture supernatant was collected and filtered through a Millipore filter (pore size: 0.45 μm). Then, the filtrate was dispensed in small amounts, and kept at −80° C. Using rat cytokine measurement ELISA kit (Biosource), the concentrations of the various cytokines in the culture supernatant were quantified.

Example 2

Production of Kupffer Cells from Cattle Liver

Figure 8:
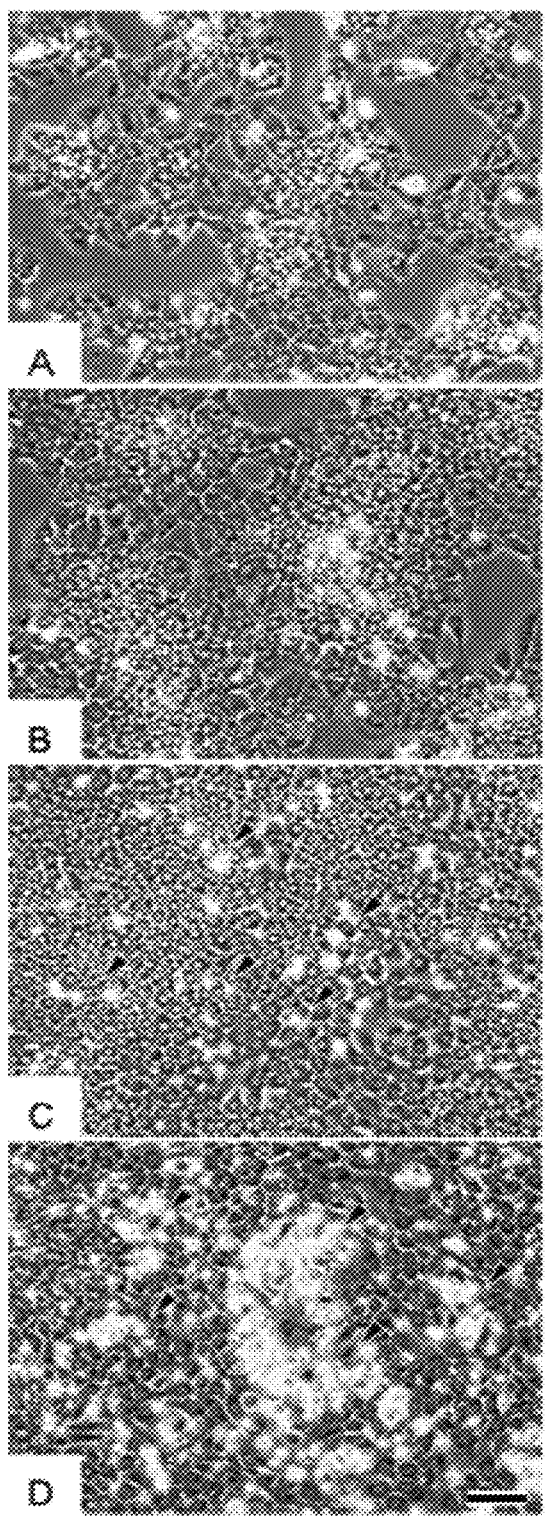
FIG. 8 shows phase-contrast microphotographs of a primary culture of hepatic parenchymal cells. The cells were derived from cattle. The observations were made 2 days (A), 4 days (B), 8 days (C), and 16 days (D) after the primary culture was started. The arrowheads indicate macrophage-like cells proliferating on fibroblast-like cells. The scale bar represents 100 μm.

By the same production method as for the above-described rat Kupffer cells, hepatic parenchymal cells were separated from the livers of calves, and $5 \times 10^6$ of the cells were seeded into each tissue culture flask (bottom area: 75 cm$^2$) for primary culture. In this primary culture, the hepatic parenchymal cells became absent substantially at week 1 to day 10. A fibroblast-like cell layer was formed at day 8 to week 2. Spherical macrophage-like cells actively proliferated on the layer (FIG. 8). In other words, at day 8 to week 2 after the primary culture was started, a mixed culture system including the fibroblast-like cells and the macrophage-like cells was formed in the tissue culture flask.

Figure 9:
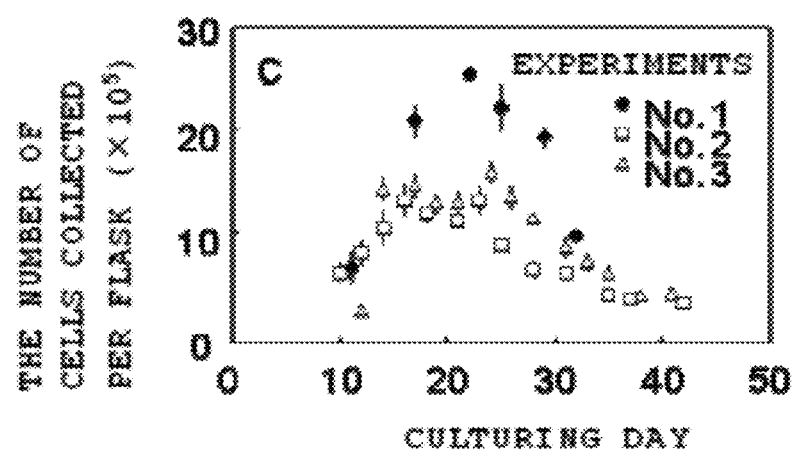
FIG. 9 is a graph showing a relationship between a culturing day and a cell count number of collected Kupffer cells in a mixed culture system using a T-75 tissue culture flask (bottom area: 75 $cm^2$). The cells were derived from the cattle.
Figure 10:
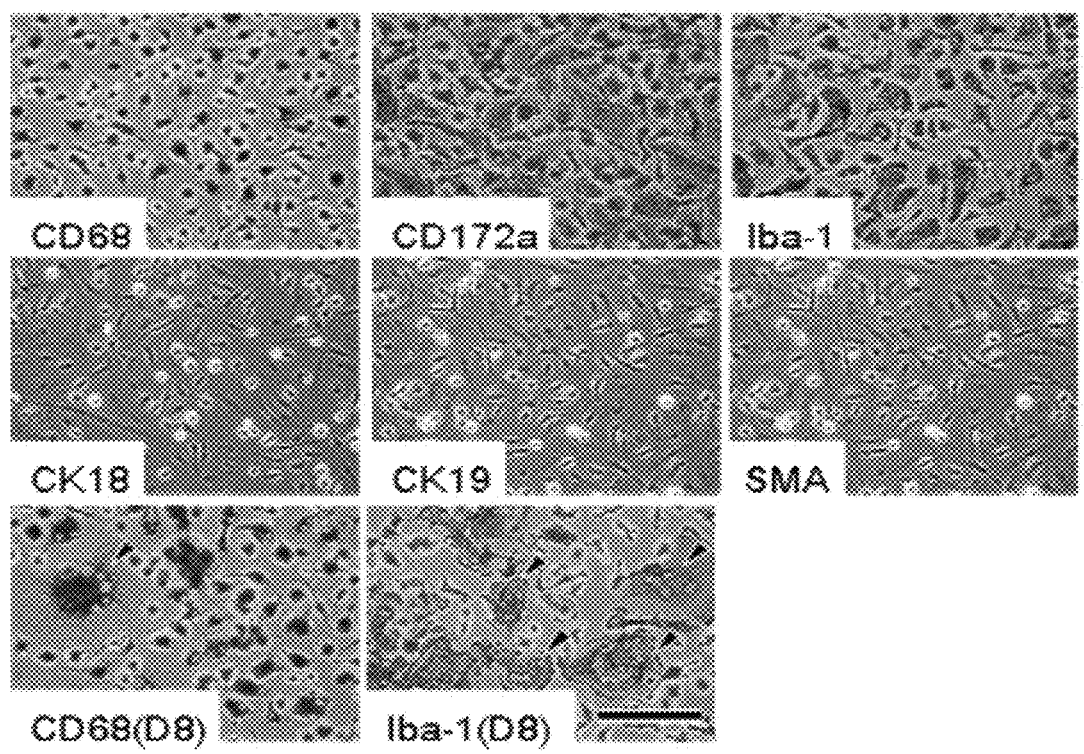
FIG. 10 shows microphotographs showing the result of immunostaining Kupffer cells selected and collected on the basis of the adherence to a plastic dish. The cells were derived from the cattle. "D8" indicates that the cells used were obtained by further culturing the selected cells for 8 days. The arrowheads indicate cells recognized as being formed into multinucleated cells. The scale bar represents 100 μm.

In the same manner as for the rat, cells were selected and collected on the basis for the adherence to the plastic dish (FIG. 9). The collected cells showed quite a similar morphology to that of a macrophage. Almost all the cells were strongly immunostained with anti-CD68 mouse monoclonal antibody (manufactured by DAKO), anti-CD172a mouse monoclonal antibody (manufactured by VMRD) or anti-Iba-1 rabbit polyclonal antibody (manufactured by Wako Pure Chemical Industries, Ltd.), but not immunostained with anti-cytokeratin 18 (CK18) mouse monoclonal antibody (manufactured by Millipore Corporation), anti-cytokeratin 19 (CK19) mouse monoclonal antibody (manufactured by Progen Biotechnik GmbH) and anti-smooth muscle actin (SMA) mouse monoclonal antibody (manufactured by Progen Biotechnik GmbH) (FIG. 10). From the above result, since cells positive for cytokeratin and smooth muscle actin were hardly found in these cell populations, it was inferred that the collected cells were contaminated with quite a small number of other cell types such as hepatic parenchymal cells and mesenchymal cells.

Figure 11:
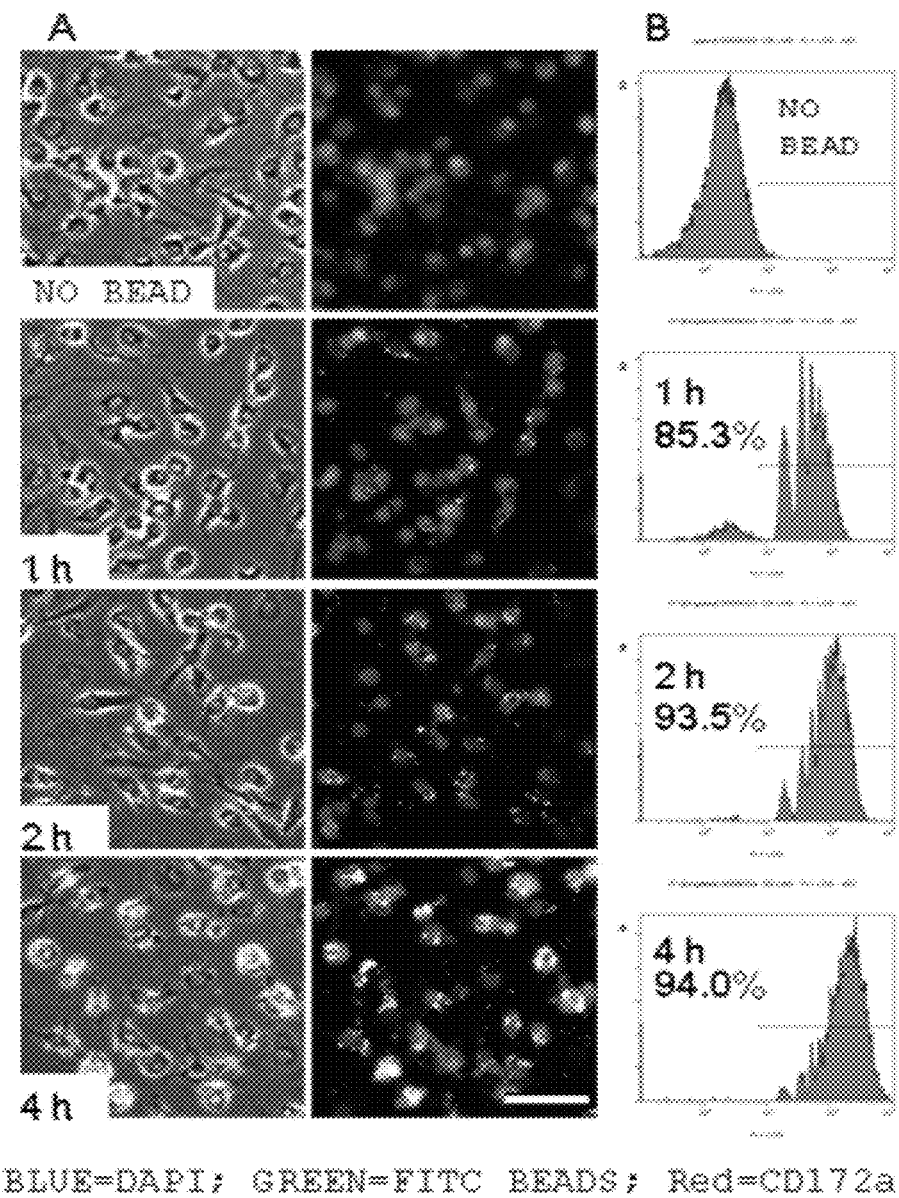
FIG. 11 shows (A) fluorescence microphotographs and (B) graphs of FACS analysis, showing the result of detecting incorporation of FITC fluorescent dye-labeled latex beads by Kupffer cells (38 days after the primary culture was started) selected and collected on the basis of the adherence to the plastic dish. The cells were derived from the cattle. The scale bar represents 50 μm.
Figure 12:
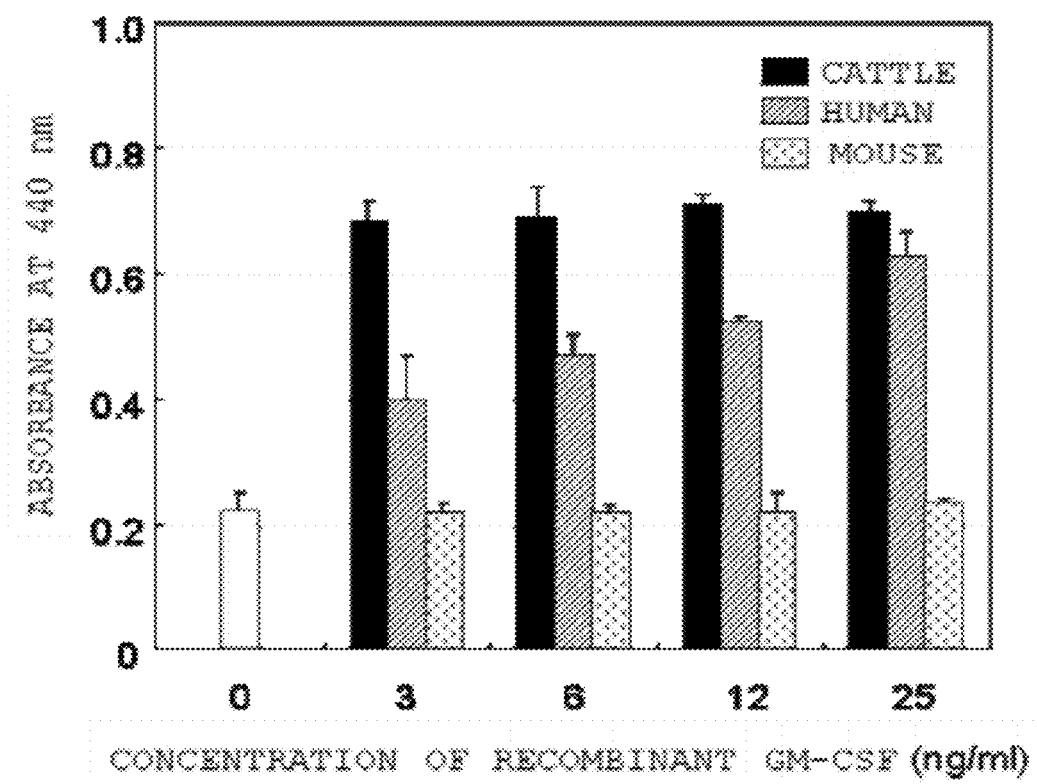
FIG. 12 is a graph showing the result of detecting the proliferative response to a recombinant cytokine (cattle, human, or mouse-derived rGM-CSF) by Kupffer cells (28 days after the primary culture was started) selected and collected on the basis of the adherence to the plastic dish. The cells are derived from the cattle.
Figure 13:
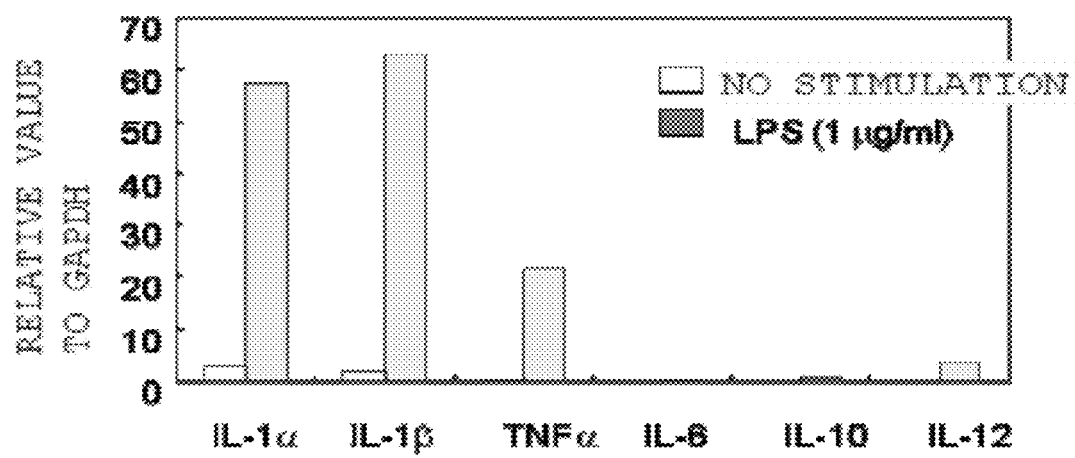
FIG. 13 shows the result of detecting gene expression of an inflammatory or anti-inflammatory cytokine upon stimulation with a lipopolysaccharide by Kupffer cells (17 days after the primary culture was started) selected and collected on the basis of the adherence to the plastic dish. The cells were derived from the cattle.

Further, as in the above-described case for the rat, the ability to form multinucleated cells (FIG. 10), the ability to phagocytose FITC fluorescent dye-labeled latex beads (FIG. 11), and the proliferative response to recombinant cytokine (rGM-CSF) (FIG. 12) were recognized. Moreover, the productivity of an inflammatory or anti-inflammatory cytokine upon stimulation with a lipopolysaccharide (FIG. 13) was also recognized.

Approximately $1 \times 10^6$ Kupffer cells were collected per tissue culture flask having a bottom area of 75 cm$^2$ by one-time collection (FIG. 9) (a total number of the cells obtained during the entire culturing period was approximately $1 \times 10^7$). It was confirmed by the same immunostaining method as for the rat that the purity of the collected Kupffer cells was 98% or higher.

The Kupffer cells collected by the above-described method were suspended in a cell-cryopreservation solution (Cell Banker 1, Juji Field Inc.) at a density of approximately $3 \times 10^6$/ml. Then, each 1-ml suspension was dispensed into a freezing vial, followed by frozen in a freezer at $-80°$ C. Thereafter, the vial was transferred into liquid nitrogen and cryopreserved (for approximately 2 years). The vial was immersed in warm water at 37° C. and rapidly thawed, and immediately thereafter a culture solution (15 ml) was added thereto. After a portion of the cell suspension was taken and mixed with an equivalent amount of trypan blue staining solution (0.5%), live cells (not stained with trypan blue) and dead cells (stained blue) were counted using a hemocytometer. As a result, the ratio of the live cells was 84%. Approximately 75% of the cells cryopreserved per vial were collected as the live cells.

From the above result, as in the case for the rat, the Kupffer cells were also separated conveniently and efficiently from the primary culture system of the calf hepatic parenchymal cells, demonstrating that the present method was applicable to a wide range of mammals.

Note that in this Example, the immunostaining as well as the measurements of the ability to phagocytose FITC fluorescent dye-labeled latex beads, the proliferative response to the recombinant cytokine (rGM-CSF), and the productivity of the inflammatory cytokine upon stimulation with the lipopolysaccharide were performed by the same method as that in Example 1.

In the measurement of the productivity of the inflammatory or anti-inflammatory cytokine, the isolated macrophage-like cells were stimulated with the lipopolysaccharide for 3 hours, and the expressions of various genes were measured by quantification real-time PCR.

Example 3

Primary Culture of Mouse liver Cells, and Immortalization of Kupffer Cells

Figure 14:
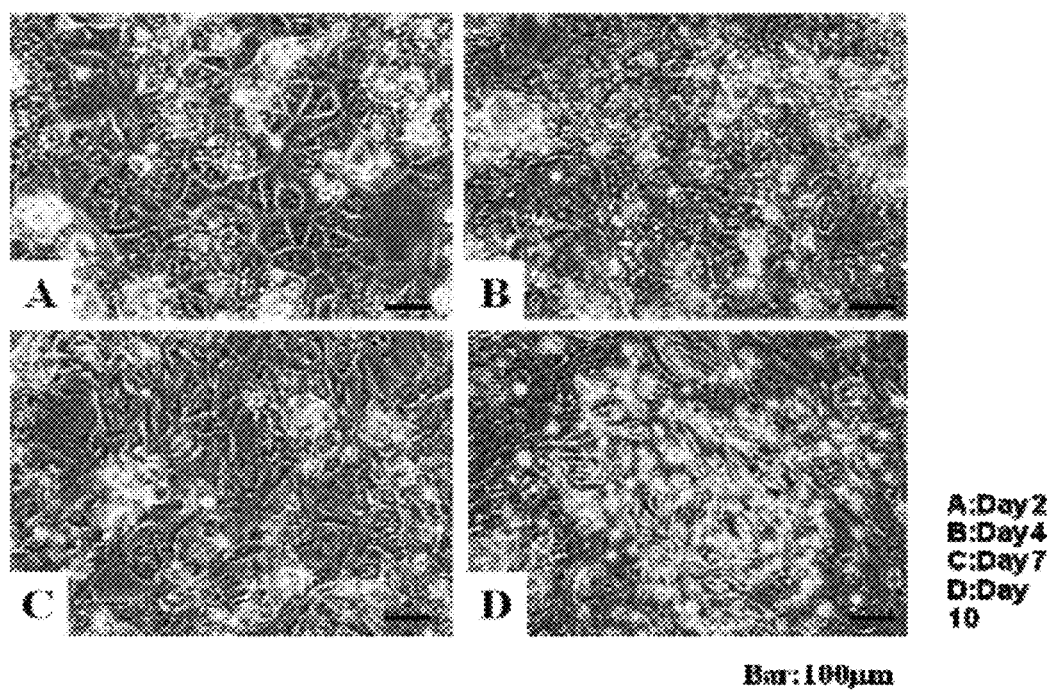
FIG. 14 shows phase-contrast microphotographs of a primary culture of hepatic parenchymal cells. The cells were derived from mice. The observations were made 2 days (A), 4 days (B), 7 days (C), and 10 days (D) after the primary culture was started. The scale bar represents 100 μm.

In the same manner as for the rat, hepatic parenchymal cell fractions were obtained from C57BL/6 mice (male, 7 weeks old). Each of the fractions was seeded into a tissue culture flask (bottom area: 25 cm$^2$). The medium used was the same as that for the rat. In this primary culture, the hepatic parenchymal cells became absent substantially at day 5 to day 7. A fibroblast-like cell layer was formed at day 7 to day 14. Spherical macrophage-like cells actively proliferated on the layer (FIG. 14).

In the same manner as in the cell immortalization method described in the known documents (Non Patent Literatures 7, 8), the cells were infected with a retrovirus vector containing a human oncogene c-myc and a neomycin resistance gene from day 11 after the culturing consecutively for 3 days (FIG. 15A). After the infection, the cells were returned to a normal medium, and the culturing was continued using a tissue culture flask (bottom area: 25 cm$^2$). At 5 to 6 days after the infections, the tissue culture flask was shaken, and thereby Kupffer cells were dissociated and caused to adhere to a plastic dish. Cells other than the Kupffer cells were washed away with PBS (FIG. 15B). The culturing was continued with a medium supplemented with an antibiotic (neomycin), and only cells into which the human oncogene c-myc gene was introduced were selectively allowed to proliferate (FIG. 16). After a cloning operation, an immortalized murine Kupffer cell line was obtained.

In the thus established murine immortalized Kupffer cell line, all the cells were strongly stained with macrophage-specific monoclonal antibodies (Mac-1, F4/80, KT022) (FIG. 17). Moreover, most of the cells proliferated as mononuclear cells, and quite occasionally cells having 2 to 4 nuclei were observed.

INDUSTRIAL APPLICABILITY

As described above, the present invention makes it possible to efficiently produce a large amount of high-purity Kupffer cells from a mammalian liver. Kupffer cells are closely associated with induction and onset of liver dysfunction, hepatitis, and cirrhosis. Thus, Kupffer cells are an important target for elucidating the liver disease state, developing therapeutic drugs therefor, and so forth. Moreover, a Kupffer cell produced by the method of the present invention is usable as a carrier of a DDS preparation for delivering a desired drug or the like to a liver by causing the Kupffer cell to possess the drug and utilizing the delivering ability to the liver. Thus, the present invention can greatly contribute not only to the use as a research tool targeting elucidation of the biological properties of Kupffer cell, but also to the use in the medical field.

The invention claimed is:

1. A method for producing Kupffer cells, comprising the steps of:
   (a) performing a primary culture of a cell population comprising at least hepatic parenchymal cells and Kupffer cells derived from a mammalian liver at least until the hepatic parenchymal cells are substantially absent, and the Kupffer cells appear and proliferate; and
   (b) collecting Kupffer cells thus proliferated.

2. The method for producing Kupffer cells according to claim 1, wherein
   the step (b) of collecting the Kupffer cells is performed by:
      shaking the culturing vessel performing the primary culture; and
      collecting Kupffer cells dissociated into a culture solution by the shaking.

3. The method for producing Kupffer cells according to claim 2, further comprising;
   placing the collected dissociated Kupffer cells in a plastic container and selecting and collecting cells adherent to the plastic container.

4. The method for producing Kupffer cells according to claim 1, wherein the Kupffer cells are collected at day 8 or later after the primary culture is started.

5. The method for producing Kupffer cells according to claim 1, wherein
   the Kupffer cells are collected 1) during the period after the Kupffer cells proliferate until the proliferation of the Kupffer cells ceases, or 2) during the period after the proliferation of the Kupffer cells ceases.

6. The method for producing Kupffer cells according to claim 1, wherein the Kupffer cells are collected between day 8 and day 20 after the primary culture is started.

7. A method for producing immortalized Kupffer cells, comprising the steps of:
   (a) producing Kupffer cells by the method according to claim 1; and
   (b) performing an immortalization treatment on the produced Kupffer cells.

8. A method for evaluating whether or not a test compound influences a biological activity of Kupffer cells, comprising the steps of:
   (a) producing Kupffer cells by the method according to claim 1;
   (b) bringing a test compound into contact with the produced Kupffer cells; and
   (c) detecting a biological activity of the Kupffer cells.

9. A method for producing a drug delivery system (DDS) preparation for delivering a desired drug to a liver, comprising the steps of:
   (a) producing Kupffer cells as a carrier of a DDS preparation by the method according to claim 1; and
   (b) causing the produced Kupffer cells to possess a drug desired to be delivered to a liver.

* * * * *